US00PP36843P2

(12) United States Plant Patent
Postill

(10) Patent No.: US PP36,843 P2
(45) Date of Patent: Jul. 22, 2025

(54) ***MAHONIA* PLANT NAMED 'HILLMAH'**

(50) Latin Name: *Mahonia eurybracteata*
Varietal Denomination: HILLMAH

(71) Applicant: Hillier Nurseries Ltd, Romsey (GB)

(72) Inventor: Alan Postill, North Baddesley (GB)

(73) Assignee: Hillier Nurseries LTD (GB)

( * ) Notice: Subject to any disclaimer, the term of this patent is extended or adjusted under 35 U.S.C. 154(b) by 0 days.

(21) Appl. No.: 18/938,443

(22) Filed: Nov. 6, 2024

(30) Foreign Application Priority Data

Apr. 12, 2024 (QZ) ..... PBR 2024/0853

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

PUBLICATIONS https://ace.media/press-releases/Qgyz (Retrieved from the Internet on Jan. 23, 2025).*

* cited by examiner

*Primary Examiner* — Susan McCormick Ewoldt
(74) *Attorney, Agent, or Firm* — Cassandra Bright

(57) ABSTRACT

A new and distinct cultivar of *Mahonia* plant named 'HILLMAH' is disclosed, characterized by large, early-blooming yellow flower spikes, followed by blue-black berries. Eye-catching architectural foliage is deep red in spring and summer, turning dark green in summer and autumn. The new variety is a *Mahonia*, typically produced as an outdoor ornamental plant.

4 Drawing Sheets

Latin name of the genus and species: *Mahonia eurybracteata.*

Variety denomination: 'HILLMAH'.

BACKGROUND OF THE INVENTION

The new cultivar is the product of an open-pollination conducted by the inventor at a nursery in Romsey, United Kingdom during 2013. The seed parent is the *Mahonia eurybracteata* 'Soft Caress' U.S. Plant Pat. No. 20,183. The pollen parent is unknown. The new cultivar 'HILLMAH' was discovered by the inventor in 2019 at the same location in Romsey, United Kingdom.

The first asexual reproduction was performed by vegetative cuttings in 2019, at the same nursery in Romsey, United Kingdom. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'HILLMAH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HILLMAH.' These characteristics in combination distinguish 'HILLMAH' as a new and distinct *Mahonia* cultivar:

1. Eye-catching architectural foliage. Young leaves are deep red in spring and summer, turning dark green in summer and autumn.
2. Compact plant habit.
3. Large yellow flower spikes from late August into November, followed by blue-black berries.
4. No thorny foliage, easy to touch.
5. Naturally well-branched, very dense foliage.
6. Evergreen, year-round interest.

PARENT COMPARISON

Plants of the new cultivar 'HILLMAH' are similar to the seed parent in most horticultural characteristics. 'HILLMAH', however, differs in the following:

1. Flower spikes of the new variety are larger than flower spikes of the seed parent.
2. Spring growth color of the new variety is deep red, while the spring growth color of the seed parent is green.
3. Foliage color of the new variety is darker green than the foliage color of the seed parent.
4. Leaves of the new variety are narrower than leaves of the seed parent.
5. Plants of the new variety are bushier than plants of the seed parent.
6. Plants of the new variety flower earlier than plants of the seed parent.

COMMERCIAL COMPARISONS

Plants of the new cultivar 'HILLMAH' can be compared to the commercial variety *Mahonia eurybracteata* 'MYOY', unpatented. Plants of these cultivars are similar in most horticultural characteristics, however, 'HILLMAH' differs in the following:

1. Flower color of the new variety is yellow, while the flower color of this comparator is more orange-yellow.
2. Spring growth color of the new variety is deep red, while the spring growth color of this comparator is light bronze.
3. Foliage color of the new variety is dark green, while the foliage color of this comparator is silver-green.
4. Plants of the new variety flower earlier than plants of this comparator.

BRIEF DESCRIPTION OF THE PHOTOGRAPHS

This new *Mahonia* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Mahonia.*

DETAILED BOTANICAL DESCRIPTION

Figure 1:
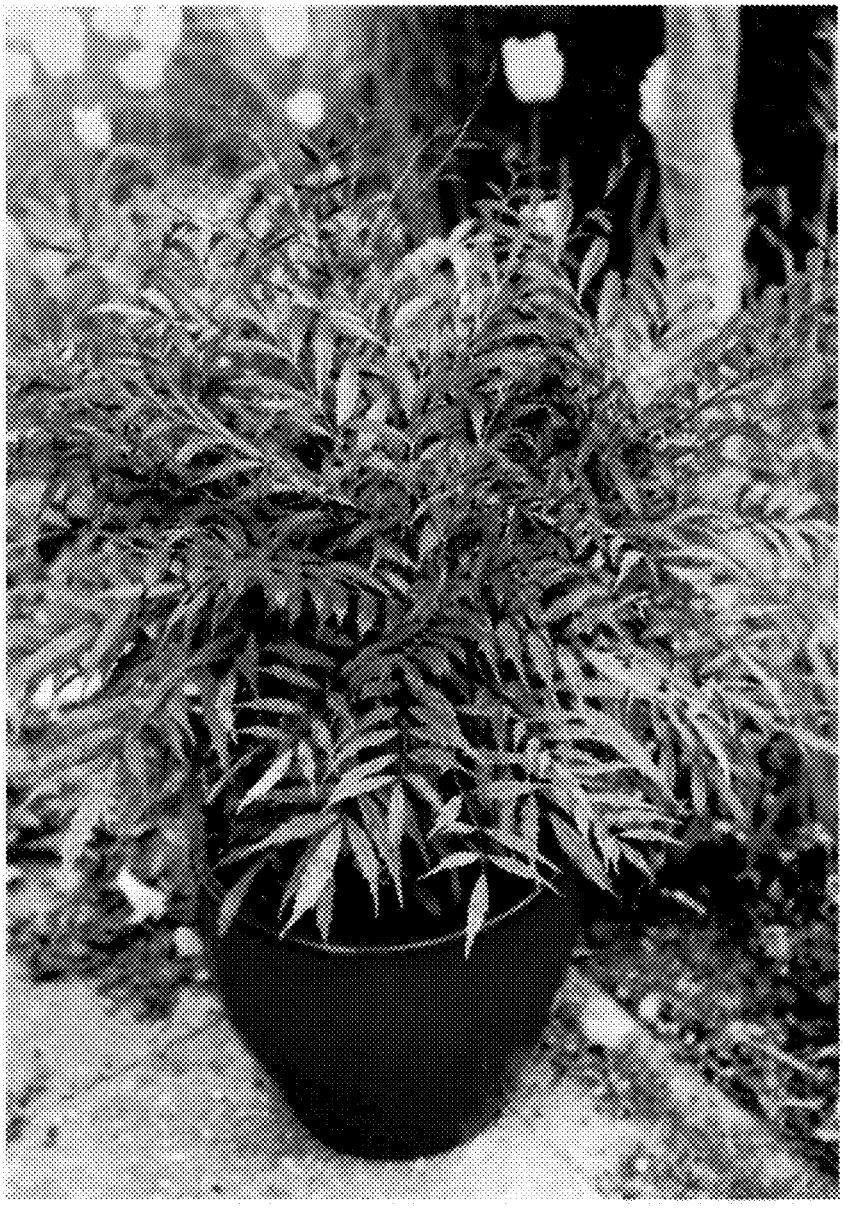
FIG. 1 is a color photograph of a plant of 'HILLMAH' during Spring, in Hampshire, UK. The plant is approximately 1.5 years old.
Figure 2:
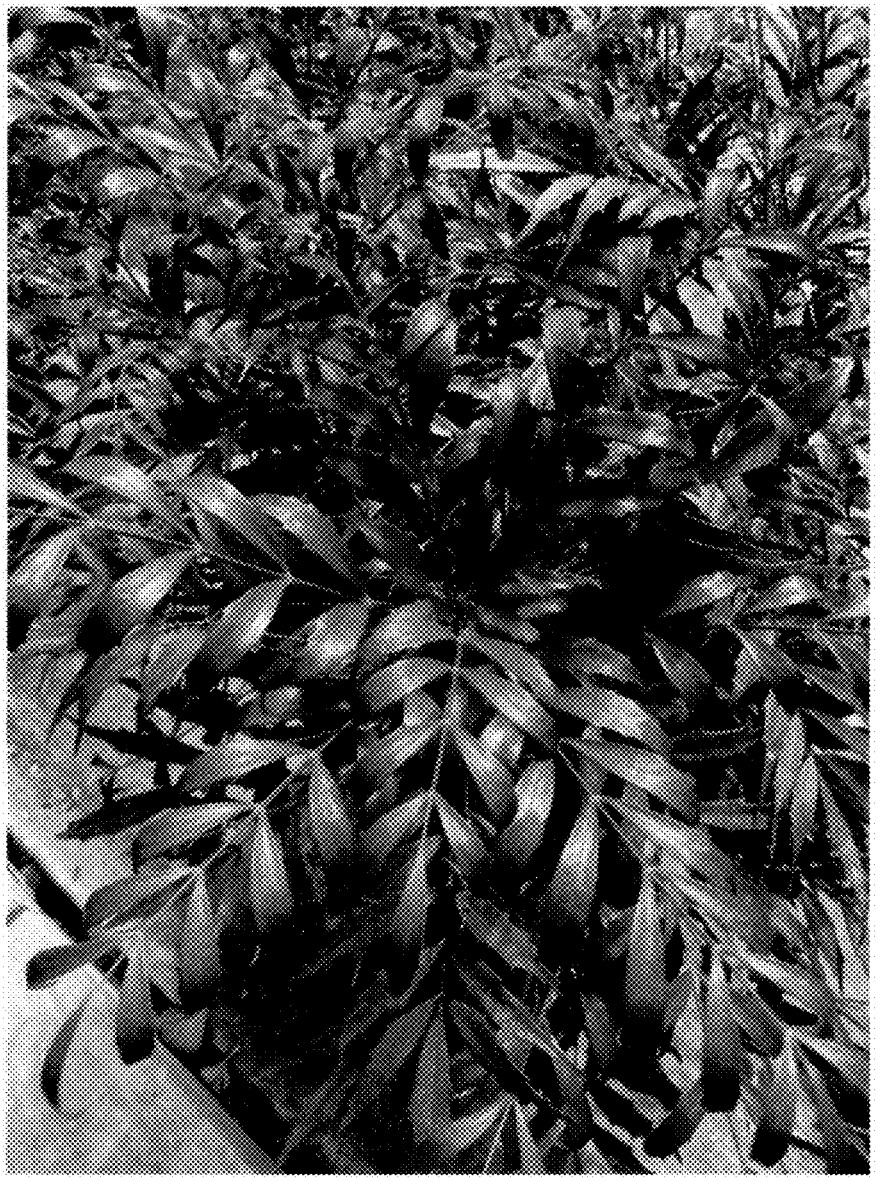
FIG. 2 is a color photograph showing a close-up view of the Spring foliage of 'HILLMAH'
Figure 3:
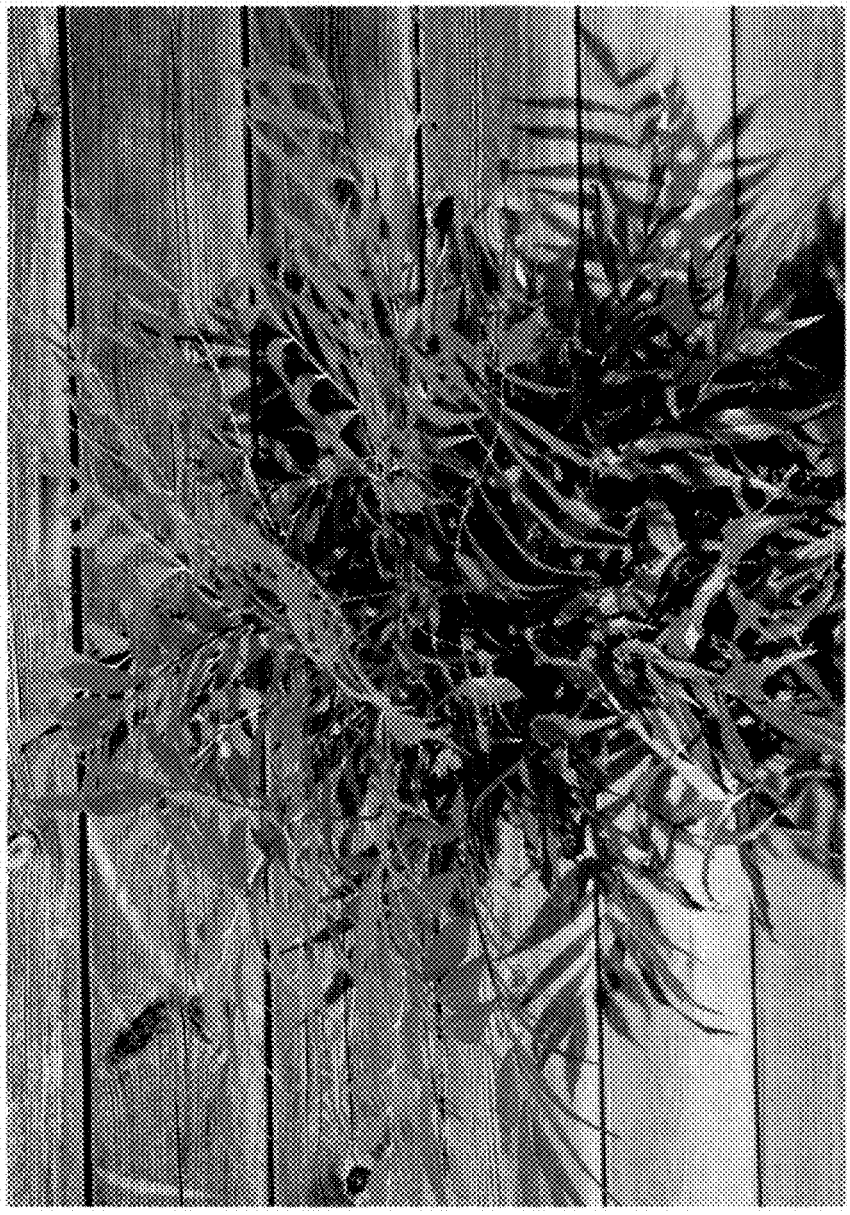
FIG. 3 is a color photograph of a plant of 'HILLMAH' during Summer, in Lier, Belgium.
Figure 4:
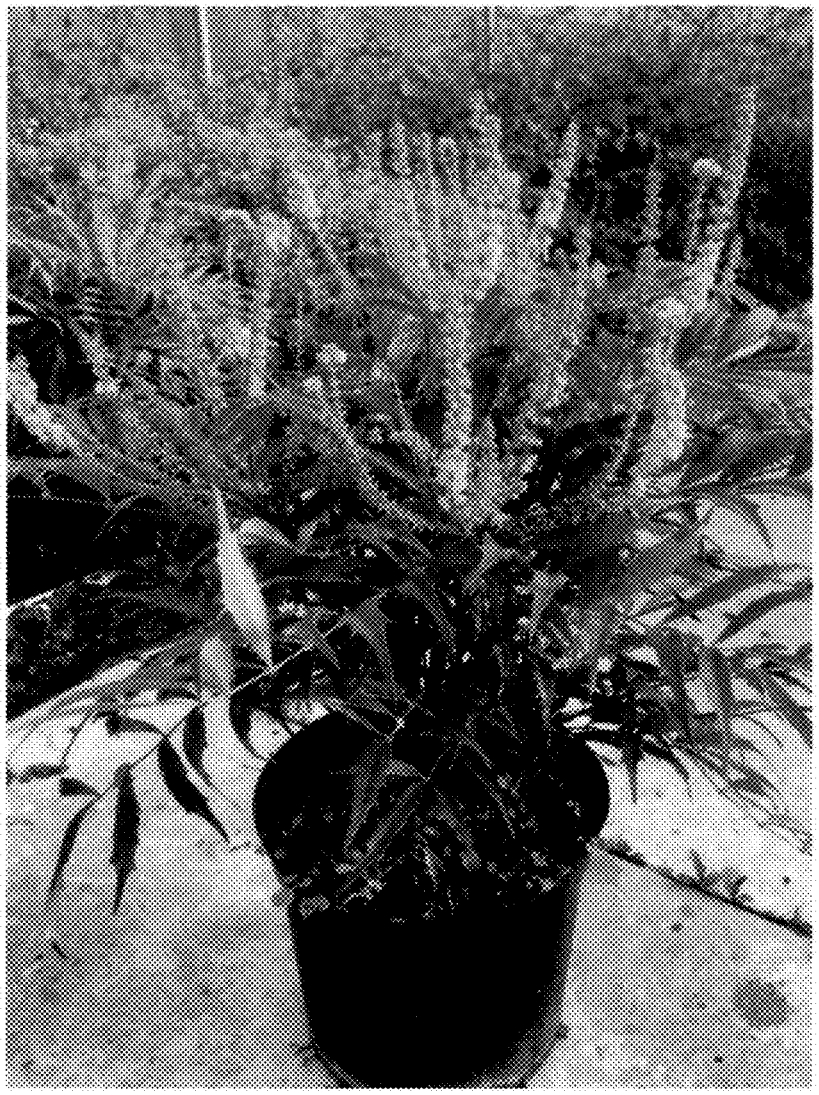
FIG. 4 is a color photograph of a flowering plant of 'HILLMAH' during Fall, in Hampshire, UK.

In the following description, color references are made to The Royal Horticultural Society Colour Chart 2015, except where general terms of ordinary dictionary significance are used. The following observations and measurements describe 'HILLMAH' plants grown in 23 cm pots in Lier, Belgium. Plants are approximately 3 years old. Temperatures ranged from approximately 3° C. to 22° C. at night and 10° C. to 32° C. during the day. No artificial light, photoperiodic treatments were given to the plants. No chemical treatments were given to plants. Measurements and numerical values represent averages of typical plant types.

Botanical classification: *Mahonia eurybracteata* 'HILLMAH'.

PROPAGATION

Method: Cuttings.
Time to rooted plug: 20 to 25 weeks.
Root description: Fleshy.

PLANT

Growth habit: Broadly spreading, evergreen, dense, woody shrub.
Height: 42 cm.
Plant spread: 56 cm.
Stem:
- *Branching habit.*—Basal.
- *Shape.*—Round.
- *Diameter.*—1.8 cm.
- *Length.*—3.8 cm.
- *Color.*—Young: RHS Yellow-Green 144C with hints of Greyed-Purple 183A. Mature: RHS Brown N199A to N199C.
- *Texture.*—Glabrous.

Internode length: About 1.5 cm.

FOLIAGE

Leaf:
- *Shape.*—Elliptical.
- *Apex.*—Acute.
- *Base.*—Attenuate.
- *Arrangement.*—Compound.
- *Quantity.*—17 leaflets per leaf.
- *Length.*—Leaf: 25 cm. Leaflet: 12 cm.
- *Width.*—Leaf: 15 cm. Leaflet: 3 cm.
- *Leaflet internode length.*—Average 3 cm.
- *Texture.*—Glabrous.
- *Margin.*—Spiny-serrate, 4 serrations per side.
- *Color.*—Young spring leaves: Upper side: Emerging RHS Greyed-Purple N186C, changing to Greyed-Purple 183A. Under side: Emerging RHS Greyed-Purple N186C, changing to Greyed-Purple 183C. Mature leaves: Upper side: RHS Green NN137B, Greyed-Purple 187B at base. Under side: RHS Yellow-Green 145A. Autumn leaves: Upper side: RHS Green 137B, Greyed-Purple 183C at base. Under side: RHS Yellow-Green 144B, Greyed-Purple 183C at base.
- *Venation.*—Pattern: Pinnate. Midrib visible on upper surface of young leaves only. Venation color: RHS Yellow-Green 144B upper surface, midrib. All other venation indistinguishable from leaf blade.

FLOWER

Natural flowering season: August to November.
Inflorescence and flower type and habit: Racemes of cup-shaped flowers.
Flowers per inflorescence: 26.
Flowers and buds per plant: About 16 flowers and 42 buds.
Inflorescence size:
- *Diameter.*—6 cm.
- *Height.*—1.5 cm.

Flower size:
- *Diameter.*—9 mm.
- *Height.*—5 mm.

Bud:
- *Shape.*—Conical.
- *Length.*—4 mm.
- *Diameter.*—3 mm.
- *Apex.*—Acute.
- *Color.*—Near RHS Yellow-Green N144D, with Orange-Red 34B and Yellow 12A.

Petals:
- *Arrangement.*—2 whorls of 6.
- *Shape.*—Obovate to oblong.
- *Quantity.*—6.
- *Length.*—3 mm.
- *Diameter.*—1.5 mm.
- *Texture.*—Glabrous.
- *Apex.*—Retuse.
- *Base.*—Square.
- *Margin.*—Entire.
- *Color.*—RHS Yellow 4A, both sides.

Sepals:
*Arrangement.*—2 whorls of 3 petaloid sepals.
*Shape.*—Obovate.
*Length.*—4 mm.
*Width.*—2 mm.
*Apex.*—Round.
*Base.*—Attenuate.
*Margin.*—Entire.
*Texture.*—Glabrous.
*Color.*—Upper surface: RHS Yellow 5B to 5C, fading to 4A to 4B towards base. Under surface: RHS Yellow 5A to 5B, fading to 4A to 4B towards base.
Peduncle:
*Length.*—1.5 cm.
*Diameter.*—2 mm.
*Color.*—RHS Yellow-Green 145C.
Pedicel:
*Length.*—2 to 3 mm.
*Diameter.*—1 mm.
*Texture.*—Glabrous.
*Color.*—RHS Yellow-Green 145C.
Brachts:
*Shape.*—Ovate.
*Length.*—2 mm.
*Diameter.*—1 mm.
*Apex.*—Acute.
*Texture.*—Glabrous.
*Color.*—RHS Yellow 5A to 5B, with Orange-Red 34B at apex.
Fragrance: Very light.

REPRODUCTIVE ORGANS

Stamens:
*Stamens number.*—6.
*Filament.*—Length: 1 mm. Width: 0.5 mm. Color: RHS Yellow 4C.
Anther:
*Length.*—1 mm.
*Width.*—0.5 mm.
*Color.*—RHS Yellow 4C.
Pollen:
*Quantity.*—Low.
Pistil: None found.

OTHER CHARACTERISTICS

Fruit: Ovoid berry, approximately 4 mm in length and 4 mm in diameter. Colored RHS Blue 103D.
Seed: Not observed.
Disease/pest resistance: Neither resistance nor susceptibility to the normal diseases and pests of *Mahonia* has been observed.
Temperature tolerance: Cold hardy to −15°.
Drought tolerance: Tolerance for drought not tested.

What is claimed is:

1. A new and distinct cultivar of *Mahonia* plant named 'HILLMAH' as herein illustrated and described.

* * * * *